(12) United States Patent
Zhang et al.

(10) Patent No.: US 9,242,037 B2
(45) Date of Patent: Jan. 26, 2016

(54) FLOW SENSOR FOR MEDICAL PUMP

(71) Applicant: Zyno Medical, LLC., Natick, MA (US)

(72) Inventors: Mei Zhang, Sharon, MA (US); Chao Young Lee, Weston, MA (US)

(73) Assignee: Zyno Medical, LLC, Natick, MA (US)

( * ) Notice: Subject to any disclaimer, the term of this patent is extended or adjusted under 35 U.S.C. 154(b) by 40 days.

(21) Appl. No.: 14/104,378

(22) Filed: Dec. 12, 2013

(65) Prior Publication Data

US 2014/0171869 A1   Jun. 19, 2014

Related U.S. Application Data

(60) Provisional application No. 61/736,784, filed on Dec. 13, 2012.

(51) Int. Cl.
*A61M 5/142*  (2006.01)
*A61M 5/168*  (2006.01)

(52) U.S. Cl.
CPC ......... *A61M 5/14228* (2013.01); *A61M 5/1689* (2013.01); *A61M 2205/3317* (2013.01)

(58) Field of Classification Search
CPC .......... A61M 5/14228; A61M 5/1689; A61M 2205/3317
USPC .................................................. 604/251–253
See application file for complete search history.

(56) References Cited

U.S. PATENT DOCUMENTS

| | | | | |
|---|---|---|---|---|
| 4,137,940 A | * | 2/1979 | Faisandier | 137/486 |
| 4,583,975 A | * | 4/1986 | Pekkarinen et al. | 604/253 |
| 5,135,485 A | * | 8/1992 | Cohen et al. | 604/67 |
| 6,562,012 B1 | * | 5/2003 | Brown et al. | 604/253 |

* cited by examiner

*Primary Examiner* — Manuel Mendez
(74) *Attorney, Agent, or Firm* — Boyle Fredrickson, S.C.

(57) ABSTRACT

A medical pump or the like provides a flow sensor element that may be integrated into the IV tubing assembly. The flow sensor element fits within the medical pump which may provide for capacitive plates sensing changes in the electrical environment within the flow sensor element to deduce flow. For example, the flow sensor element may promote free space liquid drops that cause a periodic change in capacitance across the flow sensor element or the flow sensor element may hold a physical turbine or the like whose movement changes the capacitance across the capacitive plates.

5 Claims, 3 Drawing Sheets

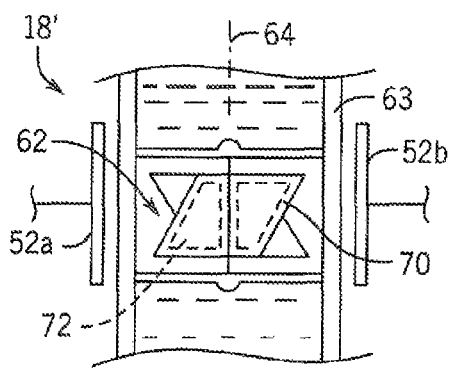
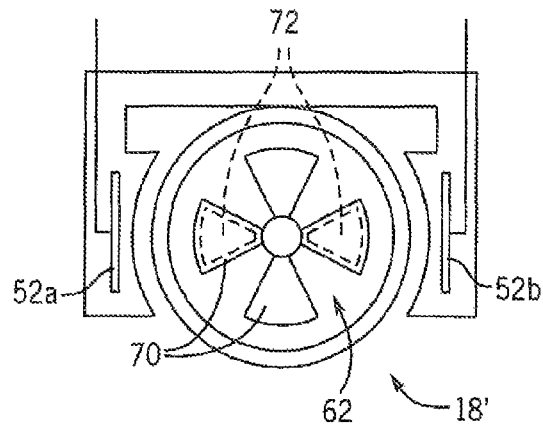
FIG. 5a  FIG. 5b
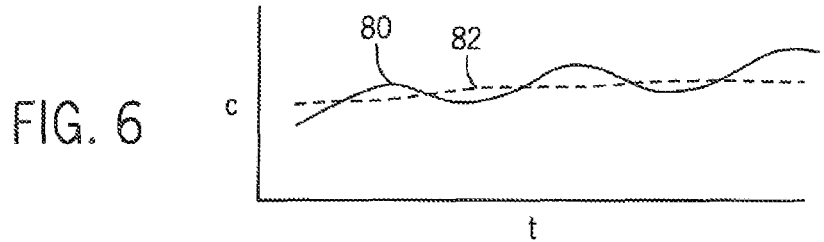
FIG. 6
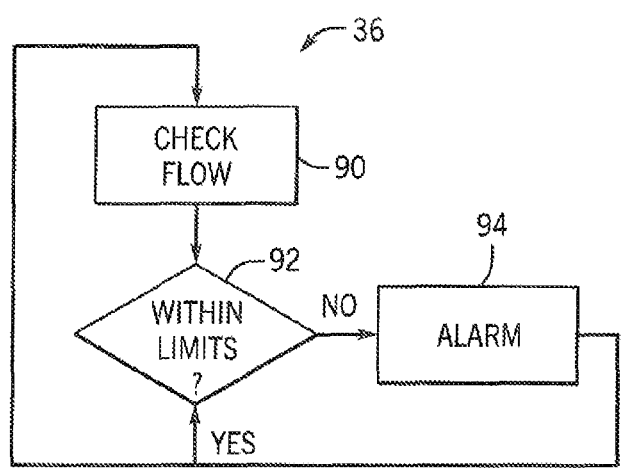
FIG. 7

FLOW SENSOR FOR MEDICAL PUMP

CROSS REFERENCE TO RELATED APPLICATION

This application claims the benefit of U.S. Provisional application Ser. No. 61/736,784 filed Dec. 13, 2012 and hereby incorporated by reference.

BACKGROUND OF THE INVENTION

The present invention relates to medical pumps for the delivery of medicines to patients with controlled rates and dosages and, in particular, to a flow sensor for characterizing the flow of medicines from such pumps.

Medical pumps, such as syringe pumps or peristaltic infusion pumps, are known for computer-controlled delivery of medication or contrast agents (henceforth drugs) to patients over a period of time. Typically, the drug is provided in a syringe (for a syringe pump) or a flexible bag (for peristaltic infusion pump) that may be connected to an IV line attached to a needle for insertion into the patient.

When a nurse or other health care professional ministering to the patient receives the drug, the healthcare professional reviews the drug description for correctness and enters the desired dose and rate into the pump. The syringe or IV line must then be mechanically connected to the pump mechanism and the mechanism activated to begin pumping.

During the pumping operation, the flow drug may be automatically monitored by one or more sensors that detect proper operation of the medical pump. Such sensors may for example, measure line pressure, the presence of bubbles in the drug, and the like.

Knowledge of the actual flow rate of the drug in the IV line is helpful in confirming proper dose and delivery rate. To some extent, the flow rate may be deduced from the operation of the pump mechanism which provides a mechanical metering; however, even in this case, independently measured flow rate upstream or downstream of the pump may be useful to determine blockages and proper pump operation.

Measuring the flow rate of the drug is complicated by the need to preserve a sterile and typically disposable conduit for the drug and by the extremely low flow rates incident to such drug delivery.

SUMMARY OF THE INVENTION

The present invention provides a flow sensor suitable for a wide range of flow rate measurements in sterile environments associated with medical drug delivery that employs a capacitive sensing element operating through sealed walls of the drug delivery conduit.

In a first embodiment, the invention provides a drip chamber positioned between capacitive sensor elements, the latter which may detect the passage of individual drug droplets falling through the drip chamber from outside of the drip chamber.

In a second embodiment, the invention provides a low inertia turbine whose rotational rate may be detected by capacitive sensor elements positioned adjacent to the turbine but again from outside the turbine chamber.

In both cases, a sterile environment is preserved for the drug delivery pathway and a wide range of flow rate may be measured.

More specifically, in a first embodiment, the invention provides a medical liquid delivery system having a housing adapted to receive an IV line having a series connected flow sensing element so that the flow sensing element fits in a housing portion. Capacitive sensor electrodes are positioned in the housing portion adjacent to the flow sensor when the flow sensor is received in the housing portion and control electronics communicate with the capacitive sense electrodes to sense flow of a medical liquid through the flow-sensor element according to capacitive changes sensed by the capacitive sensor electrodes.

It is thus a feature of at least one embodiment of the invention to provide an IV pump or similar device with an electronic sensor for low volume flows that occur with such equipment. By employing capacitive sense electrodes, flow sensing may occur through a sterile envelope of the flow sensing element without problems of contamination.

The control electronics may detect periodic fluctuations in capacitance between the capacitive sensor electrodes to sense flow as a function of frequency of the periodic fluctuations.

It is thus a feature of at least one embodiment of the invention to provide a simple sensing mechanism that avoids problems of calibration by counting fluctuations rather than equating specific capacitance levels to specific flow rates.

The control electronics may further include an alarm providing an alarm output to a user according to sensed flow.

It is thus a feature of at least one embodiment of the invention to provide the ability to automatically monitor the flow in a low flow IV type system to provide flow rate alarm signals.

The medical liquid delivery system may further include a pump positioned on the housing to receive a portion of the IV line to provide a metering/pumping of medical liquid in the IV line.

It is thus a feature of at least one embodiment of the invention to provide a flow sensor that may augment the metering capabilities of the pump, for example, to provide pump diagnosis or to detect other flow problems.

The pump may provide a metering/pumping of the medical liquid in the IV line by peristaltic compression of the IV line.

It is thus an object of the invention to provide a flow sensor that may work with a sterile chain of IV line and flow sensing elements. A peristaltic pump, like the capacitive sensing of this embodiment, may work through the sterile envelope of the IV tube.

The flow sensing element may provide a sterile electrically-insulating shell surrounding an inner chamber, the shell providing attachment points to respective ends of the first and second IV line portions, respectively, at upper and lower ends of the sterile shell, the attachment points providing liquid-tight conduits between the ends of the first and second IV line portions and the inner chamber.

It is thus a feature of at least one embodiment of the invention to separate the elements of the flow sensor into sensing electrodes and a separate sterile shell to permit the latter portion to be disposable for improved management of sterility.

The shell may include an orifice opening over the inner chamber in an upper end of the shell size to produce a series of drops falling from the orifice into the inner chamber between the capacitive sense electrodes when the flow sensing element is in place within the housing portion.

It is thus a feature of at least one embodiment of the invention to provide an extremely simple flow sensing mechanism to reduce the cost of any necessary consumable elements.

Alternatively, the shell may include a turbine wheel rotating about an axis with flow of medical liquid between the attachment points of the shell wherein the turbine wheel is positioned between the capacitive sense electrodes when the flow sensing element is in place within the housing portion and wherein the turbine wheel provides a variable capacitance between the capactive sensing electrodes with rotation of the turbine wheel.

It is thus a feature of at least one embodiment of the invention to provide a flow sensing element that can accommodate different degrees of sensitivity and flow, for example, by adjustment of the turbine blade pitch.

The turbine wheel may include an electrical conductor and the variable capacitance is provided by an effective change in capactive sensing electrode spacing or, in addition or alternatively, the turbine wheel may include an electrical dielectric and the variable capacitance is provided by a change in dielectric between the capactive sensing electrodes.

It is thus a feature of at least one embodiment of the invention to provide a simple method of capacitive sensing of a rotary turbine.

The shell may be a transparent thermoplastic material.

It is thus a feature of at least one embodiment of the invention to provide for ready visual inspection of the flow sensing element, for operation in a low-cost disposable material.

The shell may be integrally attached to the IV line to form a single disposable element.

It is thus a feature of at least one embodiment of the invention to provide for an integrated element that can be used just like an IV line to provide flow sensing.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

BRIEF DESCRIPTION OF THE FIGURES

FIGS. 5a and 5b are a fragmentary front cross-sectional view and a top plan cross-sectional view, respectively, of a second embodiment of the flow sensor chamber providing a contained turbine wheel and flanking capacitive sensors when the flow sensor chamber is inserted into the pump;

FIG. 6 is a graph of capacitance over time showing detection of rotation of the turbine wheel within the flow sensor chamber;

FIG. 7 is a simplified flowchart showing use of the flow sensor to provide an alarm condition.

DETAILED DESCRIPTION OF THE PREFERRED EMBODIMENT

Figure 1:
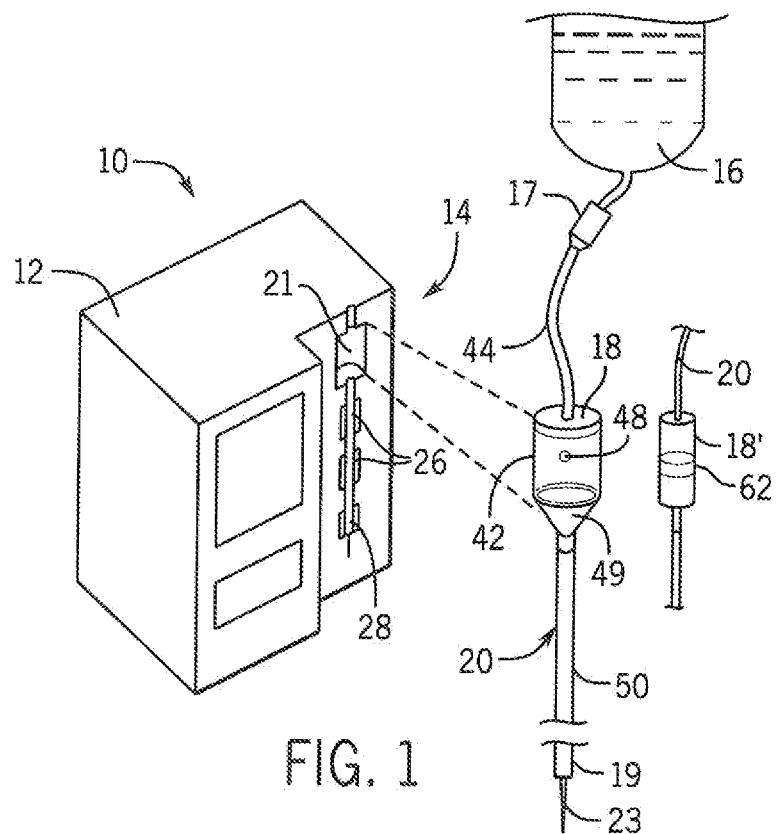
FIG. 1 is a simplified perspective representation of an example medical pump employing the sensor of the present invention for an IV line that may be contained within a portion of the pump coverable by a pump door, the IV line including an integrated flow sensor chamber per a first embodiment of the invention.

Referring now to FIG. 1, a medical pump 10, for example an infusion pump, may provide for a housing 12 incorporating a pump compartment 14 through which an IV line 20 may be threaded. The IV line 20 may communicate through a connector 17 with an IV bag 16 to a flow sensor element 18 or 18' and from the flow sensor element 18 or 18' to a connector 19 to a hypodermic needle 23 or similar connection to the patient (not shown). Generally the IV bag 16 will hold a medical fluid such as saline solution or therapeutic drug solution.

The pump compartment 14 may provide a socket 21 receiving the flow sensor element 18 or 18'. The socket 21 may be followed by peristaltic pump elements 26 through which the IV line 20 may be threaded for controllably pumping liquid therethrough according to techniques understood in the art. A pressure sensor 28, for example, providing for IV line pressure or a bubble sensor may be optionally placed above and/or below the pump elements 26 to also receive the IV tube therein.

Figure 2:
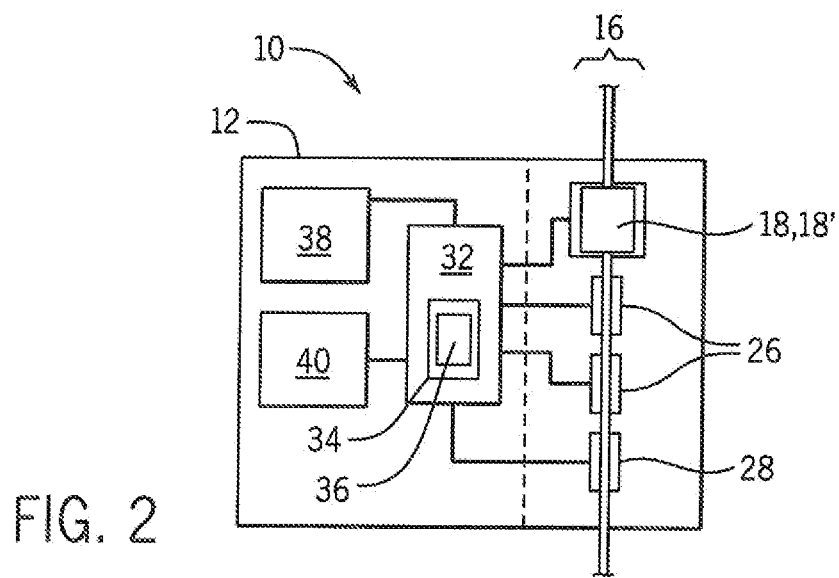
FIG. 2 is a block diagram of the principal elements of the pump including a processor for monitoring the sensor of the present invention using a stored program.

Referring now to FIG. 2, the pump 10 may include a controller 32 (which may be a microprocessor based system) having a memory 34 for holding a stored operating program 36 controlling operation of the pump 10 according to a desired dose and rate of drug delivery through the IV line 20. In particular, the controller 32 may use the data in the memory 34 to control pump elements 26 in the pump compartment 14 to provide the desired dose and delivery rate to the patient, for example, by providing successive compressing elements for peristaltically moving fluid through the IV line 20. The controller 32 may further communicate with the flow sensor element 18 of the present invention for receiving a signal therefrom as will be described. Further, the controller 32 executing the stored program 36 may read a signal from a pressure sensor 28 monitoring pressure in the IV line 20 installed in the pump compartment 14 for detection of blockage or other pumping irregularities. In addition, controller 32 may monitor other sensors (not shown) to detect bubbles in the IV line 20.

Referring still to FIG. 2, the controller 32 may also communicate with a display screen 38 for displaying various programming and operating parameters and a switch array 40 for inputting data to the controller 32, for example, for programming or initiating or stopping of the pumping action via the controller 32.

Figure 3:
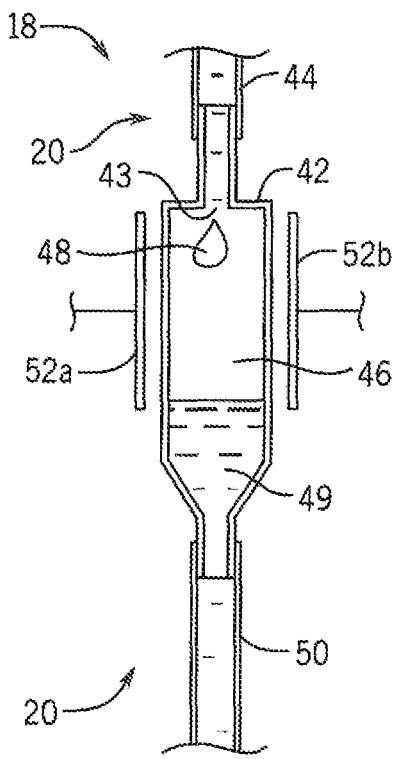
FIG. 3 is a fragmentary front elevational cross-sectional through the sensor of the first embodiment of the invention when inserted into the pump, the flow sensor chamber providing falling drops positionable between capacitor plates flanking the flow sensor chamber when the flow sensor chamber is inserted into the pump.

Referring now to FIGS. 1 and 3, in the first embodiment of the invention, the flow sensor element 18 may provide for a generally cylindrical housing 42 providing a shell defining an internal airspace 46. The cylindrical housing 42 may be constructed, for example, of a transparent, electrically insulating thermoplastic or the like, and may receive at its upper end a lower end of flexible tube 44 of the IV line 20. The cylindrical housing 42 generally provides a diameter substantially larger than the diameter of the tube 44 and may be attached to the flexible tube 44 by means of a barb, adhesive or welded connection to provide a liquid-tight conduit between the flexible tube 44 and the internal airspace 46. A connection between the tube 44 and the housing 42 further provides an orifice 43 opening into an air space 46, the orifice forming liquid from the IV bag 16 into drops 48 that may fall through the air space 46 into a pool 49 at the bottom of the cylindrical housing 42. The pool 49 may communicate through a lower end of the cylindrical housing 42 with a second tube 50 providing a drain therefrom and a continuation of the IV line 20. The second tube 50 is likewise connected in a liquid-tight seal to the cyclindrical housing in the manner described above.

When the flow sensor element 18 is placed within the socket 21, it will be flanked by first and second plates 52a and 52b positioned across a diameter of the cylindrical housing 42 and accordingly across the air space 46. The first and second plates 52a and 52b may desirably be attached to the housing 12 to maintain fixed separation and a high degree of calibration and further to separate these elements from the consumable flow sensor element 18 which is disposable.

Drops 48 passing through the air space 46 create a change in capacitance between the plates 52a and 52b caused by the increased dielectric constant of the material of the drop 48. For example, the dielectric constant of water is approximately 34 to 78 times that of air. This capacitance may be measured by a number of techniques including, for example, measurement of changes in a frequency of an oscillator incorporating the capacitance between the plates 52a and 52b into a resonant circuit or by use of the capacitance between plates 52a and 52b as part of an integrator and measuring a time constant of a ramping up of the integrator after periodic reset.

Figure 4:
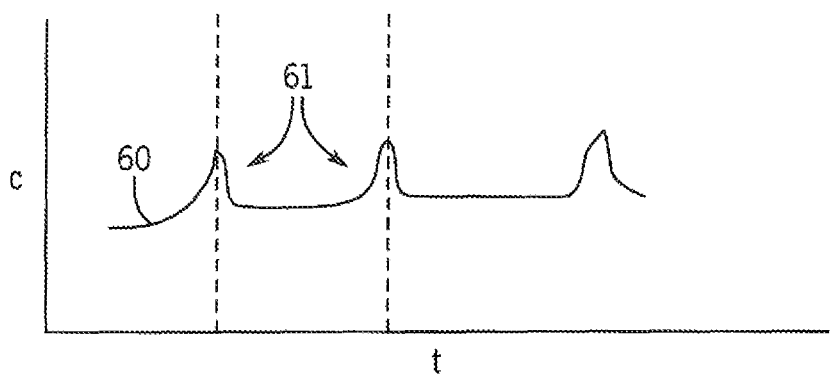
FIG. 4 is a graph of capacitance over time showing detection of falling drops within the flow sensor chamber.

Retelling now to FIG. 4, a capacitance signal 60 measuring the capacitance across plates 52a and 52b shows slight pulses 61 at the occurrence of each drop 48 passing through the air space 46 thus allowing the size and/or number of drops to be determined from the amplitude of the pulses and the accumulative volume of fluid delivered in unit time (flow rate) to be deduced. Depending on the size of the orifice 43, a relatively constant drop size will be produced so that only the number of drops per unit time needs to be measured. The pulses 61 may be detected using a threshold detector or the like after the signal 60 has been auto calibrated, for example, to have a zero average value.

In another embodiment, the size of the drops can be analyzed from images taken by an imaging device such as a CCD (Charge Coupled Device). The accumulative volume of fluid delivered in unit time (flow rate) can be deduced from the results of drop size and time interval between images.

Referring now to FIGS. 1 and 5, in a second embodiment the flow sensor element 18' may also provide for a cylindrical housing 63 of molded, transparent and electrically insulating thermoplastic. In this case the cylindrical housing 63 holds suspended therein a free spinning turbine 62 having a rotational axis 64 generally along the direction of flow and along the axis of the cylindrical housing (alternatively, the rotational axis 64 can be perpendicular to the direction of flow). The cylindrical housing 63 may be attached at its upper and lower ends to tubing 44 and 50, respectively, (as described with respect to FIG. 3) of the IV line 20. Generally, the turbine 62 provides for one or more canted blades 70 having a known pitch along a helix about the rotational axis 64 to cause a predetermined rotational rate of the turbine 62 with flow of the liquid within the cylindrical housing 63 along axis 64.

Plates 52a and 52b may flank the cylindrical housing 63 when the flow sensor element 18' is placed within the socket 21 as described above with respect to the embodiment of FIG. 3. One or more blades 70 of the turbine 62 may include high conductivity or dielectric inclusions 72, for example aluminum inserts or metal plating, that are rotationally asymmetric to change the effective spacing of the capacitor plates 52a and 52b with rotation of the turbine 62. Alternatively, a rotationally asymmetric dielectric material of the turbine blade 70 may provide for the necessary variations in capacitance between the plates 52a and 52b causing a variation in capacitance as a function of rotation of the turbine 62.

Referring now to FIG. 6, a capacitance signal 80 obtained across the capacitor plates 52a and 52b provides a time variation being a function of the rotation of the turbine 62 that may be, for example, compared to a threshold 82 for deducing the rotational rate of the turbine 62 in a manner similar to that described above. The capacitance measurement provides very little back torque on the turbine 62 (in contrast to a rotating magnet and Hall Effect sensor, for example) allowing accurate measurements of low flow rates.

Referring now to FIG. 7, flow information obtained from the flow sensor elements 18 and 18' may be provided to the controller 32 to provide alarms or feedback for the control of the pump elements 26 or to shut down operation of the pump in cases where an obstruction or misconnection may be detected. Generally, as indicated by process block 90, the stored program 36 may periodically check the flow rate and evaluate it as indicated by decision block 92 to see if it is within predefined limits. A flow rate that is too high may indicate that the IV line has been disconnected from the patient whereas a flow rate that is too low may indicate IV tube blockage or pump failure. If the flow rate is within an acceptable range, the program simply loops back to process block 90, otherwise it proceeds to process block 94 and an alarm is set, for example, as an audible tone to a user and the pump may enter a safe state, for example, shutting down operation of the pump.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

I claim:

1. A medical liquid delivery system comprising:
   a housing adapted to receive an IV line having a series connected flow sensing element so that the flow sensing element fits in a housing portion;
   capacitive sensor electrodes positioned in the housing portion adjacent to the flow sensor when the flow sensor is received in the housing portion;
   control electronics communicating with the capacitive sensor electrodes to sense flow of a medical liquid through the flow sensor element according to capacitive changes sensed by the capacitive sensor electrodes; and
   an IV line assembly including a first and second IV line portion having a series connected flow sensing element, the flow sensor element having a sterile electrically insulating shell surrounding an inner chamber, the shell providing attachment points to respective ends of the first and second IV line portions, respectively, at upper and lower ends of the sterile shell, the attachment points providing liquid-tight conduits between the ends of the first and second IV line portions and the inner chamber
   wherein the shell includes a turbine wheel rotating about an axis with flow of medical liquid between the attachment points of the shell wherein the turbine wheel is positioned between the capacitive sense electrodes when the flow sensing element is in place within the housing portion and wherein the turbine wheel provides a variable capacitance between the capacitive sensing electrodes with rotation of the turbine wheel.

2. The medical liquid delivery system of claim 1 wherein the turbine wheel includes an electrical conductor and the variable capacitance is provided by an effective change in capacitive sensing electrode spacing.

3. The medical liquid delivery system of claim 1 wherein the turbine wheel is an electrical dielectric and the variable capacitance is provided by a change in dielectric between the capacitive sensing electrodes.

4. An IV line assembly comprising:
   a first and second IV line portion having a series connected flow sensor element, the flow sensor element having a sterile shell surrounding an inner chamber, the sterile shell providing attachment points to respective ends of the first and second IV line portions, respectively, at upper and lower ends of the sterile shell, the attachment points providing liquid-tight conduits between the ends of the first and second IV line portions and the inner chamber
   wherein the shell includes a turbine wheel rotating about an axis with flow of medical liquid between the attachment points of the shell wherein the turbine wheel is positionable between capacitive sense electrodes when the flow sensing element is in place within a medical pump and wherein the turbine wheel provides a variable capacitance between the capacitive sensing electrodes with rotation of the turbine wheel.

5. The medical liquid delivery system of claim 4 wherein the turbine wheel includes at least one of an electrical conductor and the variable capacitance is provided by an effective change in capacitive sensing electrode spacing and an electrical dielectric and the variable capacitance is provided by a change in dielectric between the capacitive sensing electrodes.

* * * * *